Oct. 18, 1966 | E. FANICK | Plant Pat. 2,681
MULBERRY TREE
Filed Dec. 3, 1964 | 2 Sheets-Sheet 1
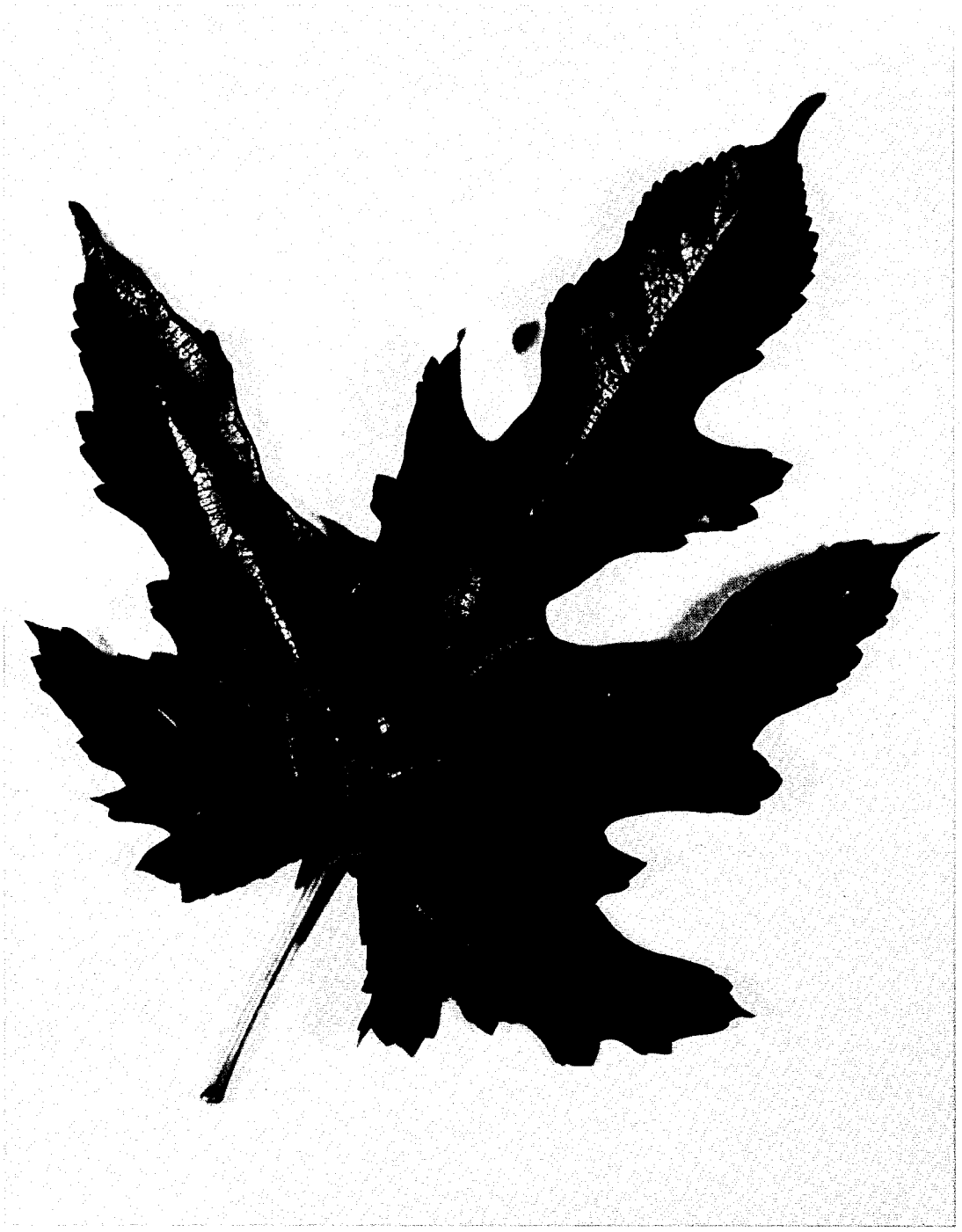
Eddie Fanick
INVENTOR
BY Browning, Simms, Hyer & Eichenberger
ATTORNEYS MULBERRY TREE
Filed Dec. 3, 1964 2 Sheets-Sheet 2
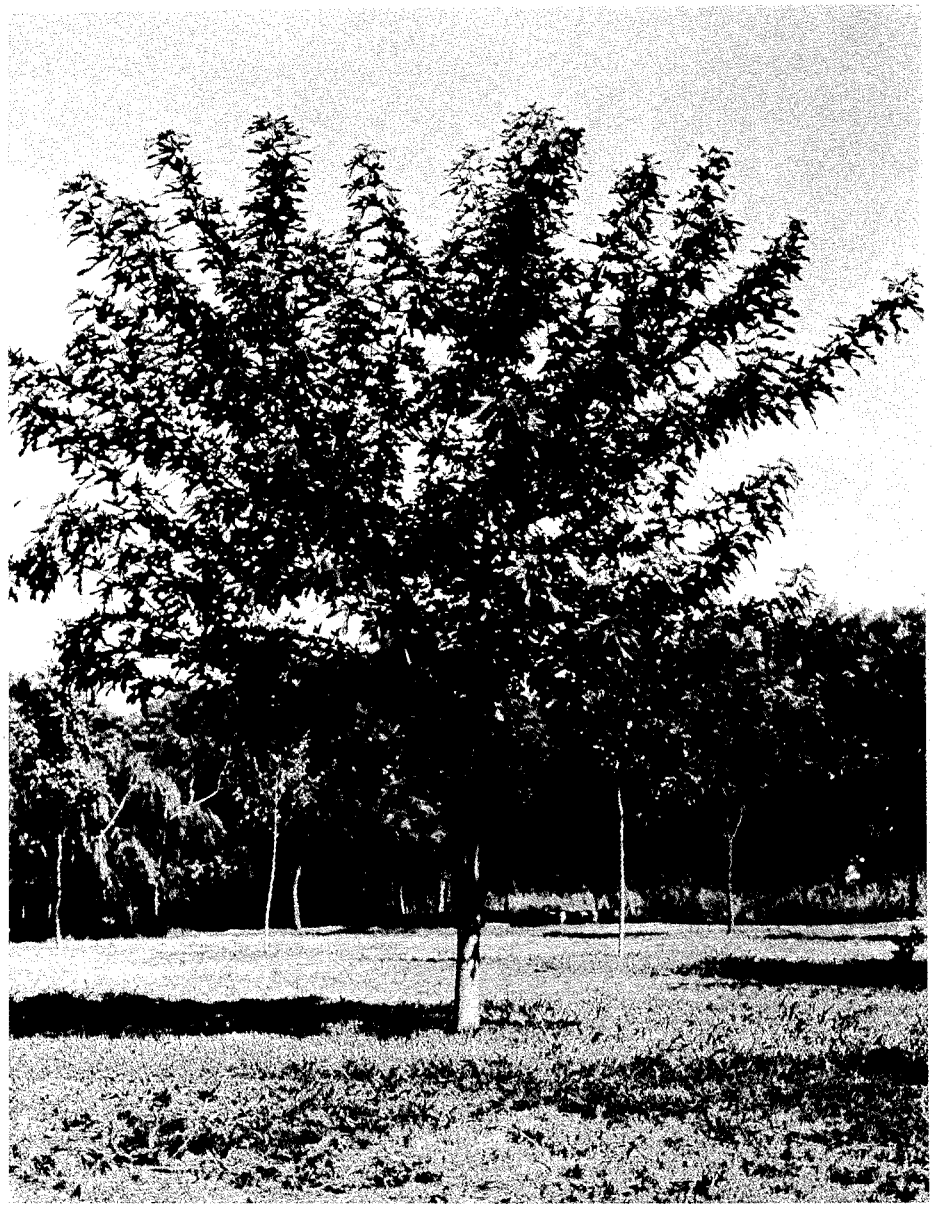
Eddie Fanick
INVENTOR
BY Browning, Simms, Hyer & Eickenroht
ATTORNEYS United States Patent Office Plant Pat. 2,681
Patented Oct. 18, 1966

2,681
MULBERRY TREE

Eddie Fanick, 1025 Holmgreen Road, San Antonio, Tex.

Filed Dec. 3, 1964, Ser. No. 415,841
1 Claim. (Cl. Plt.—33)

My new discovery is a new clone of an ornamental non-fruiting mulberry tree of the species *Morus alba*.

My new mulberry tree was discovered by me in San Antonio, Texas. A lot of *Morus alba pendula* seeds were sown by me in a cultivated area and from this sowing, I discovered the seedling of my new variety. I believe it to be a mutation.

One outstanding characteristic of my new mulberry tree is its large, deeply clefted leaves, which are lustrous and shiny dark green. Its leaves are distinctly different from other non-fruiting varieties such as *Morus alba, Morus alba striblingi, Morus alba arizona, Morus alba missali* and *Morus alba kingon* in that they are more deeply cut, stiffer, more lustrous, and a shinier green than are the leaves of these other varieties. My mulberry tree differs from the "Mapleleaf" variety mulberry tree in that it grows faster, has more upright growth, becomes dormant in the fall two or three weeks earlier, and leafs out in the spring about three weeks later. It also differs from the "Mapleleaf" variety in that every leaf is cut or clefted, whereas the "Mapleleaf" variety has many leaves with one lobe and some with two lobes growing on the same tree. The trunk is tan, lightly banded with grey.

Also, my new mulberry is a faster grower than other non-fruiting mulberry trees now in the nursery trade. It grows much taller than other species of non-fruiting mulberry trees in my arboretum.

Another important characteristic of my mulberry tree is the ease with which it may be grown and transplanted. It is compatible with most types of soils and climatic conditions. The deeply cut leaves make it an airy tree which allows filtered sunlight to grass and other plant life. It is a utility tree, ideal for modern day landscaping use as patio, play, parkway, lawn, or shelter tree.

My new mulberry tree has limbs which are stiff and do not droop and which are resistant to breakage in wind storms.

The original illustrations accompanying this specification show a full view of my new tree and also a view of one of its leaves.

Following is a detailed description of this new variety:

*Growth habit:* Similar to other ornamental non-fruiting mulberry shade trees, budde and grown by nurseries, but it is much larger and faster growing. Its growth is such that its height is substantially equal to the lateral spread of its branches. It tolerates a broad range of soils and climatic conditions. It is winter hardy to Zone 5 and possibly to much lower temperatures.

*Foliage:* Abundant but due to leaf shape, its over-all appearance is one of airiness.

*Leaves.*—Simple, palmately lobed, deeply clefted, normally quinquefid. Color: Deep green, greener than other non fruiting mulberry varieties; with the color intensified by the brilliant luster of the leaflets; closest to Monticello Green, Plate 23, 11–E, Maerz and Paul Color Dictionary, 1st Edition. Size: Averaging six inches across and eight inches long and sometimes larger. Shape: Ovate cutleaf. Texture: Stiff, lustrous and shiny. Edge: Undulate and incised. Arrangement: Alternate, internodes four to six inches.

*Petiole:* Three inches and stiff; holds leaf rigid.

*Bark:* Fissured and scaly; the color being light brown (nearest to Sudan Brown, Plate 14, 12–L, Maerz and Paul Color Dictionary, 1st Edition), banded and lightly blotched with grey (nearest to Slate grey, Plate 14, 2–A, Maerz and Paul Color Dictionary, 1st Edition).

*Reproductive organ:* My mulberry is staminate and is not fruiting or seeding as determined by observation of a specimen for five years.

I have asexually reproduced this variety of mulberry by budding in my nursery and its distinguishing characteristics have proved to be firmly fixed.

Having thus disclosed my discovery, I claim:

A new variety of non-fruiting mulberry tree (*Morus alba*), substantially as shown and described, characterized particularly by its deeply clefted, dark green, lustrous leaves; its taller and faster growth compared with other varieties of non-fruiting mulberry trees; its light brown trunk banded and blotched with grey; its limbs which are stiff and do not droop and which are resistant to breakage in wind storms; and its growth such that its height is substantially equal to the lateral spread of its branches.

No references cited.

ABRAHAM G. STONE, *Primary Examiner.*

R. E. BAGWILL, *Assistant Examiner.*